United States Patent
Shaheen et al.

(10) Patent No.: US 6,361,787 B1
(45) Date of Patent: *Mar. 26, 2002

(54) ENHANCED ANTIMICROBIAL COMPOSITION

(75) Inventors: Elias A. Shaheen, Walnut Creek; Judy Y. Ikawa, Hayward; Robert L. Blum, Concord, all of CA (US)

(73) Assignee: The Clorox Company, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/085,340

(22) Filed: May 27, 1998

(51) Int. Cl.$^7$ ................................................ A01N 25/32
(52) U.S. Cl. ..................... 424/406; 424/405; 510/101; 514/642; 514/643; 514/739; 514/762
(58) Field of Search ................................. 574/739, 762, 574/642, 643; 424/405, 406; 510/101

(56) References Cited

U.S. PATENT DOCUMENTS

| | | | |
|---|---|---|---|
| 4,113,709 A | | 9/1978 | Quinlan |
| 4,214,909 A | * | 7/1980 | Mawatari et al. ............. 106/16 |
| 4,540,505 A | | 9/1985 | Frazier |
| 4,867,898 A | | 9/1989 | Spaulding et al. |
| 5,116,602 A | | 5/1992 | Robinson et al. |
| 5,135,743 A | | 8/1992 | Stanislowski et al. |
| 5,256,401 A | | 10/1993 | Duckenfield et al. |
| 5,424,059 A | | 6/1995 | Prencipe et al. |
| 5,575,652 A | | 11/1996 | Gaffar et al. |

FOREIGN PATENT DOCUMENTS

| | | |
|---|---|---|
| DE | 19523320 | 2/1997 |
| EP | 0065725 | * 12/1982 |

* cited by examiner

*Primary Examiner*—Neil S. Levy
(74) *Attorney, Agent, or Firm*—Joel J. Hayashida; Alison De Runtz

(57) ABSTRACT

The present invention provides an improved antimicrobial composition which includes at least one quaternary ammonium compound and nerolidol. The nerolidol component of the composition provides enhanced antimicrobial efficacy, even when used in small amounts. Further, the nerolidol component provides such enhanced antimicrobial efficacy that the quaternary ammonium compound may be used in reduced amounts as compared to the amounts used for antimicrobial effect in prior formulations. The enhanced antimicrobial composition of the present invention is especially useful in cleaning or disinfecting applications, such as the cleaning of hard surfaces.

11 Claims, No Drawings

ENHANCED ANTIMICROBIAL COMPOSITION

FIELD OF THE INVENTION

The present invention relates generally to antimicrobial compositions and, more particularly, to improved antimicrobial compositions including an enhancing, potentiating or synergistically effective component. The inventive compositions are particularly useful in disinfecting and cleaning applications, such as the disinfecting and cleaning of hard surfaces.

BACKGROUND OF THE INVENTION

Disinfecting compositions which include a variety of active disinfecting components, such as aldehydes, glycols, amines and quaternary ammonium compounds, are known. For example, laid-open patent application specification, DE 195 23 320 A1, of Bode et al., discloses a disinfecting concentrate which contains such disinfectants, conventional additives, water, and one or more terpenes in a particular concentration, namely, 0.1 to 50 percent by weight relative to the concentrate. The terpene additive is said to enhance the efficacy of the disinfectants in the concentrate. The concentrate is disclosed as being useful for the disinfection of instruments, for disinfection in the presence of mycobacteria and certain viruses, and, upon dilution, for the disinfection of surfaces. While Bode et al. disclose a variety of terpene additives, they do not disclose the sesquiterpene alcohol, nerolidol, as being useful in their disinfecting concentrate.

In U.S. Pat. No. 5,135,743, Stanislowski et al. disclose a composition for deodorizing animal wastes in which a liquid dispersion of pine oil and boric acid act to prevent ammonia formation. Adjunct materials, such as quaternary ammonium compounds, can be included in the composition. The pine-oil component is said to be a complex blend of a variety of organic compounds, including terpenes. Stanislowski et al.'s pine-oil component does not contain nerolidol, however, as this particular sesquiterpene alcohol is not derived from pine oil.

In U.S. Pat. No. 4,867,898, Spaulding et al. disclose a liquid, hard-surface cleaner, which contains pine oil, but no quaternary ammonium compounds. Spaulding et al. teach against the use of quaternary ammonium compounds in cleaners because of the undesirable qualities of these compounds, such as high residue deposition after cleaning, toxicity, and irritation to a user's skin, eyes, and the like. As with Stanislowski et al.'s pine-oil composition, Spaulding et al.'s pine-oil cleaner does not contain nerolidol.

U.S. Pat. No. 4,540,505 to Frazier discloses that cleansing agents containing a germicidally effective quaternary ammonium compound are known, as are cleansing agents containing the terpene derivative d-limonene. However, Frazier discloses that when even a small amount of d-limonene is introduced into a composition having a cleansing agent containing a quaternary ammonium compound, the composition is destabilized. Thus, Frazier discloses a composition including monoethers of certain aliphatic glycols to provide composition clarity and stability.

In U.S. Pat. No. 4,113,709, Quinlan discloses certain polymers of quaternary thiazines as being useful for a variety of applications, including the inhibition of corrosion. Quinlan further discloses that these polymers may be blended with known acid inhibitors, such as quaternary ammonium compounds or synergists, which may include terpene alcohols. Use of the term "synergist" is not explained.

Nerolidol is not disclosed in any of the above-referenced patents. It is disclosed, however, in relation to various oral compositions in a number of United States patents. For example, U.S. Pat. No. 5,116,602 to Robinson et al. discloses nerolidol as a sesquiterpene alcohol flavor component in an oral antiplaque composition. The flavor component is said to provide antimicrobial activity at low concentrations.

U.S. Pat. No. 5,256,401 to Duckenfield et al. discloses nerolidol as an effective antiplaque agent in a mouthwash composition. The effectiveness of the substantially water-insoluble antiplaque agent is said to be attainable without the excessive presence of solvent to solubilize the agent and without the use of an antibacterial-enhancing agent.

As a further example, U.S. Pat. No. 5,424,059 to Prencipe et al. discloses nerolidol as a water-insoluble, non-cationic antibacterial agent useful in an antiplaque dentifrice. The effectiveness of the antibacterial agent is said to be enhanced by xylitol.

Finally, U.S. Pat. No. 5,575,652 to Gaffar et al. discloses that both non-cationic antibacterial agents and cationic antibacterial agents, such as quaternary ammonium compounds, have been investigated as antiplaque agents. Gaffar et al. note that while the non-cationic agents can be compatible with anionic components, the most investigated of the cationic agents have proved to be generally ineffective when used with anionic materials in an oral composition. They thus disclose nerolidol as a water-insoluble, non-cationic antibacterial agent useful in an oral gel composition applied to dental implant sites. The effectiveness of the antibacterial agent is said to be realized when the agent is solubilized in the presence of an antibacterial-enhancing agent.

Prior to the present invention, it was not known or suspected that nerolidol, in combination with at least one quaternary ammonium compound, provides an antimicrobial composition with significantly enhanced antimicrobial efficacy as compared to prior antimicrobial compositions. Further, it was not known or suspected that nerolidol, when so used, allows for a reduction in the amount of quaternary ammonium compound which would otherwise be necessary for such antimicrobial efficacy.

SUMMARY OF THE INVENTION

It is an object of the present invention to provide an improved antimicrobial composition which shows enhanced antimicrobial efficacy. This and other objects are achieved by the present invention, which provides an improved antimicrobial composition by virtue of a nerolidol component. The nerolidol component is a surprisingly effective enhancer or potentiator of antimicrobial efficacy.

More particularly, it has been discovered that nerolidol significantly enhances the antimicrobial efficacy of a composition containing at least one quaternary ammonium compound. This enhanced anti-microbial efficacy is obtained with a surprisingly small amount of nerolidol.

That is, in standard tests for efficacy against various microorganisms, the inventive composition shows significantly reduced number of positive results as compared to a formulation containing a quaternary ammonium compound, but lacking nerolidol. These enhanced-efficacy results were obtained using minimal amounts of nerolidol, for example, 0.01 or 0.02 weight percent of the enhancer relative to the inventive composition.

In further efficacy tests, it was determined that nerolidol does not enhance the antimicrobial efficacy of a commercial pine cleaner formulation which does not contain a quaternary ammonium compound. It is theorized that nerolidol enhances or potentiates antimicrobial efficacy of the quaternary ammonium compound of the inventive composition, perhaps via synergism, although this invention is not in any way limited to this or any other theory.

As the nerolidol enhances antimicrobial efficacy, the amount of quaternary ammonium compound in the inventive composition may be much less than that used in prior compositions. For example, a typical prior art composition (not having the benefit of nerolidol) contains quaternary ammonium compounds in an amount more than about 1.1 weight percent relative to the composition. By contrast, in the present invention, positive results were obtained from efficacy tests performed with an inventive composition having reduced amounts of the quaternary ammonium compound, for example, 0.87 weight percent of such compound relative to the inventive composition.

The use of reduced amounts of quaternary ammonium compound constituents is important for environmental reasons, such as compliance with the standards of the U.S. Environmental Protection Agency for hard-surface disinfectants, and for consumer protection reasons, such as the reduction or elimination of skin or eye irritation which is particularly important for household cleaning compositions. Further, the use of reduced amounts of quaternary ammonium compound constituents improves the anti-filming and anti-streaking characteristics of the inventive compositions, which are particularly desirable in compositions for the cleaning of hard surfaces.

In summary, the test results evidence the significant enhanced antimicrobial efficacy of the inventive composition including at least one quaternary ammonium compound and nerolidol. This enhanced efficacy may be obtained using surprisingly small amounts of the enhancing or potentiating nerolidol. Further, this enhanced efficacy may be obtained using reduced amounts of quaternary ammonium compounds, as compared to amounts used in prior formulations.

Additional objects, advantages and features of the various aspects of the present invention will become apparent from the following description of its preferred embodiments.

DESCRIPTION OF PREFERRED EMBODIMENTS

In the present invention, it has been discovered that an antimicrobial composition which includes at least one quaternary ammonium compound and nerolidol, exhibits enhanced antimicrobial efficacy. The inventive composition is particularly effective in the disinfecting of a surface, such as a hard surface exposed to contamination by microorganisms.

As used herein, unless otherwise specified or understood, the term "antimicrobial", the term "antibacterial", and like terms refer to the capacity to inhibit or to destroy bacteria, fungi and viruses on objects or surfaces; the term "disinfecting" and like terms refer to the capacity to eliminate many or all pathogenic microorganisms, with the exception of bacterial endospores, on objects or surfaces; and the term "sanitizing" and like terms refer to the capacity to reduce contaminants on objects or surfaces to levels considered safe according to a public health ordinances, or the capacity to reduce a bacterial population by significant numbers where public health requirements have not been established (for example, for contact surfaces in non-food environments, a 99.9% reduction in the bacterial population is sufficient, and for contact surfaces in food environments, a 99.999% reduction in the bacterial population is sufficient). Thus, in terms of the categories of efficacy used herein, relative to one another, antimicrobial efficacy is broad, sanitizing efficacy is intermediate, and disinfecting efficacy is narrow.

More particularly, it has been discovered that the nerolidol component of the inventive composition is a surprisingly effective enhancer or potentiator of antimicrobial efficacy. The enhancing or potentiating effect of nerolidol in the inventive composition is believed to involve synergism, although the invention is not in any way limited to synergistic activity.

Merely by way of convenience, terms such as enhancing, potentiating, and synergistically effective, are used interchangeably in the description of the present invention, unless indicated otherwise. As used herein, an enhancer, potentiator, or synergistically effective component of the inventive composition, is any chemical agent that boosts the antimicrobial efficacy of another antimicrobial substance of the composition.

Table 1 lists components of the inventive composition and the concentration ranges for same in approximate weight percentages (%) relative to the inventive composition, according to a preferred embodiment.

TABLE 1

| Component | Weight Percent (%) |
|---|---|
| Quaternary Ammonium Compound[1] | 0.50–5.00 |
| Nerolidol | 0.01–2.00 |
| d-Limonene | 1.00–5.00 |
| Dipropylene Glycol n-Butyl Ether | 0.00–5.00 |
| Isopropyl Alcohol | 1.00–7.00 |
| Linear Alcohol Ethoxylate $C_{10-12}$[2] | 2.00–8.00 |
| Linear Alcohol Ethoxylate $C_{10-12}$[3] | 1.00–6.00 |
| Water and Optional Additive(s) | Remainder |

[1]Dialkyl Dimethyl Ammonium Chloride
[2]8 moles Ethoxylate
[3]2.6 moles Ethoxylate As indicated in Table 1, an optional additive, such as a fragrance, a dye or coloring agent, or a combination of same, may be included in the inventive composition. The inventive composition may be formulated such that it "blooms", or becomes cloudy, when it is combined with water, to signal to the user that the composition is ready for use.

The inventive composition may be formulated quite simply, either by combination to form a relatively homogeneous composition, as is preferred, or by initial separation of certain components, for example, in a multi-chamber apparatus, wherein the initially separated components are combined upon delivery to form the composition. These variations are described below.

In the preferred case, the homogeneous composition may be formed by adding the components in any order and mixing them to form a microemulsion of a continuous or aqueous phase and a disperse or oil phase in which the nerolidol is dispersed. For example, the inventive composition may be so formulated to form a microemulsion having an aqueous phase which is from about 60 to about 98 weight percent relative to the composition and an oil phase which is from about 2 to about 40 weight percent relative to the composition.

As used herein, the term "microemulsion" is used to refer to a stable mixture of an aqueous phase and an oil phase, the latter having dispersed oil droplets of a diameter on the order of less than or equal to about 100 nanometers. In the preferred inventive composition, the oil phase is comprised of at least the d-limonene, nerolidol, linear alcohol ethoxylate $C_{10-12}$ (2.6 moles ethoxylate) and dipropylene glycol n-butyl ether components.

In the alternative case, the components may be separately housed until delivery, during which the inventive composition is formed. For example, the components may be separated based on compatibility considerations, such that incompatible components are separately housed, or based on convenient dilution considerations, such that a concentration of active components and a diluent or combination of diluent components are separately housed, prior to delivery. Apparatus and methods useful in this alternative case, are disclosed in co-pending United States Pat. Applications, which are incorporated herein by reference, namely, Ser. No. 08/605,824 of Choy et al., entitled "Composition and Apparatus for Surface Cleaning" and filed on Feb. 23, 1996, and Ser. No. 08/979,022 of Choy et al., entitled "Composition and Apparatus for Surface Cleaning" and filed on Nov. 26, 1997, which is a continuation of Ser. No. 08/606,822, now abandoned.

Table 2 lists components of the inventive composition and the concentration of same in approximate weight percentages (%) relative to the inventive composition, according to a particularly preferred embodiment.

TABLE 2

| Component | Weight Percent (%) |
|---|---|
| Quaternary Ammonium Compound[1] | 0.78 |
| Nerolidol | 0.10 |
| d-Limonene | 2.50 |
| Dipropylene Glycol n-Butyl Ether | 1.00 |
| Isopropyl Alcohol | 4.00 |
| Linear Alcohol Ethoxylate $C_{10-12}$[2] | 3.60 |
| Linear Alcohol Ethoxylate $C_{10-12}$[3] | 2.25 |
| Water and Optional Additive(s) | Remainder |

[1]Dialkyl Dimethyl Ammonium Chloride
[2]8 moles Ethoxylate
[3]2.6 moles Ethoxylate This preferred embodiment of the inventive composition is formulated, as described above, to form a microemulsion having an aqueous phase which is preferably about 94.15 weight percent relative to the composition and an oil phase which is preferably about 5.85 weight percent relative to the composition. While the inventive composition may be formulated to produce the above-described "bloom", this preferred embodiment is not so formulated.

Antimicrobial Components

The principal antimicrobial component of the inventive composition includes at least one quaternary ammonium compound. Preferred quaternary ammonium compound constituents include alkyl dimethyl benzyl ammonium chlorides, such as those commercially available as BTC 885 and BTC 888 from Stepan Chemical Co. of Northfield, Ill.; dialkyl dimethyl ammonium chlorides, such as those commercially available as Bardac 2050 and Bardac 2080 from Lonza, Inc. of Fair Lawn, N.J.; and poly[oxyethylene (dimethyliminio)ethylene-(dimethyl-iminio)ethylene dichlorides] such as that commercially available as Busan 77 from Buckman Labs Inc. of Memphis, Tenn. A most preferred quaternary ammonium compound is dialkyl dimethyl ammonium chloride, such as BARDAC 2050 commercially available from Lonza, Inc. The quaternary ammonium compound, or a plurality of such compounds, is used in an amount sufficient for antimicrobial efficacy in the inventive composition, such as the amounts shown in Tables 1 and 2.

In the present invention, it is desirable to use the least amount of quaternary ammonium compound possible for antimicrobial efficacy, as the use of a greater amount of such compound is more expensive, increases toxicity, or irritation to a user's skin or eyes, and/or increases deposition of residue. In hard-surface cleaning applications, residue deposition is particularly undesirable, as it results in a loss of surface shine, and consequently, consumer dissatisfaction. Preferably, the quaternary ammonium compound is used in an amount sufficient for the antimicrobial efficacy of the inventive composition, including nerolidol, which is less than that sufficient for the antimicrobial efficacy of the composition in the absence of nerolidol. A particularly preferred amount of quaternary ammonium compound is 0.78 weight percent relative to the inventive composition, as shown in Table 2.

Antimicrobial-Enhancing Component

The antimicrobial potentiator, nerolidol (3,7,11-trimethyl-1,6,10-dodecatrien-3-ol), is a sesqui-terpene alcohol which is derived from the oils of various flowers, such as orange flower, neroli, sweet orange and ylang ylang, and from balsam of Peru, which is the aromatic resin of a tropical American tree, *Myroxylon pereirae*. Nerolidol is commercially available from Givaudan-Roure of Teaneck, N.J.; BASF Corporation of Wyandotte, Michigan; Sigma of St. Louis, Mo.; and Aldrich Chemical Company of Milwaukee, Wis. In the present invention, nerolidol is used in an amount sufficient to enhance the antimicrobial efficacy of the inventive composition. That is, nerolidol is used in amount sufficient to enhance the antimicrobial efficacy of the composition, as compared to the antimicrobial efficacy of the composition in the absence of nerolidol.

Antimicrobially efficacious amounts of nerolidol are those set forth in Tables 1 and 2. It has been found that the nerolidol provides significant antimicrobial-efficacy enhancement, such that the amount of quaternary ammonium compound in the inventive composition may be lower than that which would be required if the composition lacked nerolidol. The use of a lower amount of quaternary ammonium compound in the inventive composition is advantageous in that the inventive composition may be formulated less expensively, while providing the additional advantages of significantly reduced or eliminated toxicity, or irritation to a user's skin and eyes, and significantly reduced or eliminated deposition of residue, such as the deposition of residue on hard surfaces.

Other Components

Other components of the inventive composition, according to the preferred embodiments described in Tables 1 and 2, are described in turn below. By way of convenience, but not by way of limitation, a component having multiple functions, for example, solvency and cleaning efficacy, is described in terms of such multiple functions, but generally categorized in terms of a particular discrete function, for example, cleaning efficacy, or described as being in an amount sufficient for a particular functional efficacy, for example, an amount sufficient for cleaning efficacy, to avoid the overlapping of categories.

Preferably, d-limonene is used in the inventive composition as a solvent having cleaning efficacy. Limonene ($C_{10}$, $H_{12}$) is an active terpene which is derived from various natural oils. Limonene occurs naturally in d- and l-isomeric forms, a racemic mixture of which is dipentene. Commercial sources of d-limonene include Florachem of Jacksonville, Fla.; Glidco of Jacksonville, Fla.; and Firmenich of Safety Harbor, Fla. In the present invention, the d-limonene component is used primarily for its cleaning efficacy. That is, d-limonene is preferably used in amounts sufficient for cleaning efficacy in the inventive composition, such as the amounts shown in Tables 1 and 2. The d-limonene component is also used secondarily for its having antimicrobial efficacy and desirable odor properties. While the d-limonene component is a particularly preferred cleaning solvent, other solvents having cleaning efficacy may be used, either alone or in combination with d-limonene, as further described herein.

By way of example, dipropylene glycol n-butyl ether ("DPnB") is preferably used in the inventive composition as a solvent. DPnB also acts in the inventive composition as a cleaning solvent or grease-cutter. As such, DPnB is preferably used in amounts sufficient for cleaning efficacy, such as the amounts shown in Tables 1 and 2. While DPnB is a particularly preferred cleaning solvent, other suitable solvents may be used, either alone or in combination with DPnB, as further described herein.

Preferably, isopropyl alcohol is also used in the inventive composition as a coupling agent to increase the solubility of the oil phase of the microemulsion. Thus, it is preferably used in amounts sufficient for enhancing oil-phase solubility in the inventive composition, such as the amounts shown in Tables 1 and 2. The isopropyl alcohol may also act to clarify the composition. While isopropyl alcohol is a particularly preferred solubility enhancer, other solubility enhancers may be used, either alone or in combination with isopropyl alcohol, as further described herein.

The linear alcohol ethoxylates listed in Tables 1 and 2 are nonionic surfactants that are preferably used in the inventive composition for detergency. These preferred nonionic surfactants provide for the removal of oily soils and aid in the formation of the microemulsion of the inventive composition, and are preferably used in the amounts sufficient for soil-removing efficacy, such as those shown in Tables 1 and 2. While these linear alcohol ethoxylates are the preferred nonionic surfactants, other nonionic surfactants may be used for detergency in the inventive composition. These other surfactants, further described herein, may be used in place of, or in addition to, either one or both of the preferred linear alcohol ethoxylates.

Preferably, water is also used in the inventive composition for appropriate dilution and for formation of the aqueous phase of the microemulsion of the inventive composition. Deionized water is preferred, although sterile distilled water or even well-water may be used.

Additives

The composition of the present invention may be formulated to include additives, such as solvents, hydrotropes, surfactants, disinfectants, chelating agents, insecticides, fungicides, rodenticides, fragrances, dyes, coloring agents, propellants, and the like, which enhance performance, stability, and/or commercial or aesthetic appeal of the compositions. Such components may be included according to compatibility, desirability, convenience, or other factors. Preferably, such components are used in amounts sufficient for functional efficacy in terms of the function they provide or for which they are employed in the inventive composition. Generally, any one of these additives is present in an amount from about 0 to about 10 weight percent of the composition.

Suitable solvents, which may be used alone or in addition to those described above, include generally water soluble or dispersible organic solvents. In formulations of the inventive composition having high water content, a dispersant, such as a hydrotrope or other emulsifier, may be added, as further described herein. As used herein, unless otherwise specified or understood, the term "hydrotrope" and the like generally refer to a non-micelle forming substance, either liquid or solid, either organic or inorganic, which is capable of solubilizing insoluble or sparingly soluble compounds in a liquid (typically, aqueous) medium. A hydrotrope suitable for use herein includes those described in U.S. Pat. No. 4,863,633, particularly, at column 8, line 20 through column 10, line 22, which is incorporated herein by this reference.

Examples of suitable cleaning solvents include pine oil. Pine oil solvents are used primarily for cleaning efficacy, and thus, are used in an amount sufficient for cleaning efficacy. These solvents may also provide some antimicrobial efficacy, in which case, they are preferably used in an amount sufficient for antimicrobial efficacy. Pine oil solvents are used secondarily for their deodorizing properties.

Further examples of suitable cleaning solvents include terpene derivatives. Terpene derivatives appropriate for use in the inventive composition include terpene hydrocarbons having a functional group, such as terpene alcohols, terpene ethers, terpene esters, terpene aldehydes and terpene ketones.

Examples of suitable terpene alcohol solvents include verbenol, transpinocarveol, cis-2-pinanol, nopol, isoborneol, carbeol, piperitol, thymol, α-terpineol, terpinen-4-ol, menthol, 1,8-terpin, dihydro-terpineol, nerol, geraniol, linalool, citronellol, hydroxycitronellol, 3,7-dimethyl octanol, dihydro-myrcenol, tetrahydro-alloocimenol, perillalcohol, and falcarindiol. Examples of suitable terpene ether and terpene ester solvents include 1,8-cineole, 1,4-cineole, isobornyl methylether, rose pyran, α-terpinyl methyl ether, menthofuran, trans-anethole, methyl chavicol, allocimene diepoxide, limonene mono-epoxide, isobornyl acetate, nonyl acetate, α-terpinyl acetate, linalyl acetate, geranyl acetate, citronellyl acetate, dihydro-terpinyl acetate and meryl acetate. Further, examples of suitable terpene aldehyde and terpene ketone solvents include myrtenal, campholenic aldehyde, perillaldehyde, citronellal, citral, hydroxy citronellal, camphor, verbenone, carvenone, dihydro-carvone, carvone, piperitone, menthone, geranyl acetone, pseudo-ionone, α-ionine, iso-pseudo-methyl ionone, n-pseudo-methyl ionone, iso-methyl ionone and n-methyl ionone. Other terpene hydrocarbons having functional groups that may be used as solvents in the inventive composition are discussed in detail in Simonsen and Ross, *The Terpenes*, Volumes I–V, Cambridge University Press, 2nd Ed., 1947, which is incorporated herein by this reference.

Other suitable solvents having cleaning or grease-cutting efficacy, include, for example, ethylene glycol monobutyl ether, ethylene glycol monopropyl ether, propylene glycol n-propyl ether, propylene glycol monobutyl ether, diethylene glycol n-butyl ether, dipropylene glycol methyl ether, and any mixture thereof Suitable coupling agents or solubility enhancers, which may be used alone or in addition to those described above, include solvents that are generally water soluble or dispersible organic solvents that have a vapor pressure of at least 0.001 mmHg at 25° C. Preferably, the solubility enhancer is selected from alkanols, $C_{1-6}$ diols, $C_{1-10}$ alkylene glycol ethers, and any mixture thereof. Suitable alkanols include, for example, methanol, ethanol, n-propanol, butanol, pentanol, hexanol, positional isomers thereof, and any mixture thereof Diols, such as methylene, ethylene, propylene and butylene glycol, may be used in addition to, or in place of, such alkanols.

Suitable surfactants, which may be used alone or in addition to those described above, include nonionic surfactants having efficacy as detergents. By way of example, suitable nonionic surfactants include linear alkoxylated alcohols, branched alkoxylated alcohols, and alkoxylated alkylphenols.

Examples of suitable alkoxylated alcohols include ethoxylated $C_{5-20}$ alcohols, propoxylated $C_{5-20}$ alcohols, and ethoxylated and propoxylated $C_{5-20}$ alcohols, having from about 1 to about 5 moles of ethylene oxide, or from about 1 to about 5 moles of propylene oxide, or from about 1 to about 5 moles of both ethylene oxide and propylene oxide, per mole of alcohol, the selection of the alkoxylated alcohol being determined according to an hydrophilic-lipophilic balance ("HLB", wherein the least hydrophilic materials have low HLB numbers, and more hydrophilic materials have higher HLB numbers) of less than about 10, and more preferably, less than about 8. Example of suitable ethoxylated alcohols include a Neodol series of ethoxylated alcohols from Texaco Chemical Co., such as Neodol 25-3 (linear $C_{12-15}$; 3 moles of ethylene oxide ("EO") per mole of alcohol; HLB of 7.8) and Neodol 91-2.5 (linear $C_{9-11}$; 2.5 moles of EO); Alfonic 1412-40 ($C_{12-14}$; 3 moles of EO) from Conoco; Surfonic L 12-2.6 ($C_{10-12}$; 3 moles of EO) and Surfonic L 24-3 ($C_{12-14}$; 3 moles of EO) from Huntsman Chemical; and Tergitol 25-L-3 ($C_{12-15}$; 3 moles of EO) from Union Carbide. Examples of suitable secondary ethoxylated alcohols include Tergitol 15-S-3 ($C_{11-15}$; 3 moles of EO) from Union Carbide.

Suitable branched surfactants include alkoxylated alcohols and alkoxylated alkylphenols, such as the preferred tridecyl ethers. By way of example, suitable alkoxylated alcohols and alkoxylated alkylphenols include tridecyl ethers, such as Trycol TDA-3 (3 moles of EO) from Henkel KGaA (formerly, Emery) and Macol TD 3 (3 moles of EO) from Mazer Chemicals, Inc., and ethoxylated nonylphenols, such as Macol NP-4 (4 moles of EO; HLB of 8.8) from Mazer Chemicals, Inc., Triton N-57 (HLB of 10.0) and Triton N-42 (HLB of 9.1) from Rohm & Haas Co., Igepal CO-520 (HLB of 10.0) from GAF Chemicals Corp., Alkasurf NP-5 (HLB of 10.0) and Alkasurf NP-4 (HLB of 9.0) from Alkaril Chemicals, Surfonic N-40 (HLB of 8.9) from Huntsman Chemical, and further examples, such as those provided in *McCutcheon's Emulsifiers and Detergents,* 1987, which is incorporated herein by this reference (note in particular, page 282).

More generally, examples of suitable surfactants include those from the Neodol series from Texaco Chemical Co., the Alfonic series from Conoco, the Surfonic series from Huntsman Chemical, the Tergitol series from Union Carbide; secondary ethoxylated alcohols from Union Carbide (for example, Tergitol 15-S-3); branched surfactants from Henkel KGaA (formerly Emery) and Mazer Chemicals, Inc. (for example, Macol TD 3); alkoxylated alkylphenols from Mazer Chemicals, Inc. (for example, Macol NP-4), Rohm & Hass Co. (for example, the Triton series), GAF Chemicals Corp. (for example, the Igepal series) and others; and other surfactants, such as those provided in *McCutcheon's Emulsifiers and Detergents,* 1987.

Nonionic, water-soluble surfactants may also be used in the inventive composition. These surfactants may be selected from, among others, ethoxylated alcohols, such as those from the Alfonic series from Conoco, such as Alfonic 1412-60 ($C_{12-14}$; 7 moles of EO); those from the Neodol series from Shell Chemical Company, such as Neodol 25-7 ($C_{12-15}$; 7 moles of EO), Neodol 45-7 ($C_{14-15}$; 7 moles of EO) and Neodol 23-5 (linear $C_{12-13}$; 5 moles of EO; HLB of 10.7); those from the Surfonic series from Huntsman Chemical Company, such as Surfonic L 12-6 ($C_{10-12}$: 6 moles of EO) and Surfonic L 24-7 ($C_{12-14}$; 7 moles of EO); and those from the Tergitol series from Union Carbide, such as Tergitol 25-L-7 ($C_{12-15}$; 7 moles of EO); ethoxylated nonylphenols, such as those from the Macol series from Mazer Chemicals, Inc., such as Macol NP-6 (6 moles of EO; HLB of 10.8), Macol NP-9.5 (9.5 moles of EO; HLB of 13.0); those from the Triton series from Rohm & Haas Co., such as Triton N-101 (9-10 moles of EO; HLB of 13.4) and Triton N-111 (HLB of 13.8); polyethoxylated nonylphenols, such as those from the Igepal series from GAF Chemicals Corp., such as Igepal CO-530 (HLB of 10.8), Igepal CO-730 (HLB of 15.0), Igepal CO-720 (HLB of 14.2), Igepal CO-710 (HLB of 13.6), Igepal CO-660 (HLB of 13.2), Igepal CO-620 (HLB of 12.6) and Igepal CO-610 (HLB of 12.2); those from the Alkasurf series from Alkaril Chemicals, such as Alkasurf NP-6 (HLB of 11.0), Alkasurf NP-15 (HLB of 15.0), Alkasurf NP-12 (HLB of 13.9), Alkasurf NP-11 (HLB of 13.8), Alkasurf NP-10 (HLB of 13.5), Alkasurf NP-9 (HLB of 13.4), and Alkasurf NP-8 (HLB of 12.0); and those from the Surfonic series from Huntsman Chemical Company, such as Surfonic N-60 (HLB of 10.9), Surfonic N-120 (HLB of 14.1); Surfonic N-102 (HLB of 13.5); Surfonic N-100 (HLB 13.3); Surfonic N-95 (HLB of 12.9); and Surfonic N-85 (HLB of 12.4).

Suitable disinfectants, which may augment the disinfecting action of the antimicrobial components, include, for example, chlorhexidine gluconate, hydrogen peroxide, sodium hypochlorite, acetic acid, benzoic acid, boric acid, citric acid, sorbic acid, and phenols, aldehydes and alcohols having disinfecting, sanitizing or antimicrobial activity.

Fragrances, such as those commercially available from Givaudan-Roure, International Flavors and Fragrances, Firmenich, Norda, Bush Boake and Allen, Quest, and others, may be included in any of the compositions produced according to the embodiments described herein. Suitable fragrances may take the form of fragrance oils. Generally, only small amounts of fragrance are needed to improve the aesthetic quality of the inventive composition. For example, a fragrance or mixture of fragrances may be present in an amount of up to, and including, about 1.0 weight percent of the composition. Preferably, a fragrance or mixture of fragrances is present in an amount from about 0.1 to about 0.5 weight percent of the composition.

Dyes, pigments and coloring agents may also be included in small amounts. By way of example, suitable dyes and colorants include those which can be solubilized or suspended in the inventive composition, such as those available from Milliken Chemicals of Spartanburg, S.C.; Pylam of Garden City, N.J.; Rhodes; Warner-Jenkinson of St. Louis, Mo.; and Hilton Davis Company of Cincinnati, Ohio. These adjuncts may be incorporated in the inventive composition in amounts of up to, and including, about 2.0 weight percent of the composition.

Another optional additive is a chelating agent, also known as a sequestrant. Most preferably, the chelating agent is an aminopolyphosphonate. The chelating agent assists in maintaining the solution stability of a liquid formulation based on its ability to tie up heavy metals or other materials which can destabilize such liquids, for example, by causing or catalyzing oxidation. Suitable aminopolyphosphonates are commercially available under the identifier, Dequest, from Monsanto Company. Examples of such aminopolyphos-phonates include Dequest 2000, 2041 and 2060. (See also U.S. Pat. No. 4,473,507 to Bossu, particularly, column 12, line 63 through column 13, line 22, which is incorporated herein by this reference.) A polyphosphonate, such as Dequest 2010, is also suitable for use. Other chelating agents, such as ethylene-diaminetetraacetic acid (EDTA) and nitrilotriacetic acid (NTA) may also be suitable for use. Still other new, preferred chelating agents are new propylene-diaminetetraacetates, such as Hampshire 1,3 PDTA from W. R. Grace, and Chel DTPA 100#F, from Ciba Geigy A. G. Mixtures of any of the foregoing may be suitable as well.

Further optional additives include a builder, a propellant, an additional disinfecting agent. Examples of suitable builders include alkaline builders, i.e., those which in aqeous solution will attain a pH of 7 to 14, preferably, 9 to 12. Examples of inorganic builders include the alkali metal and ammonium carbonates (including sesquicarbonates and bicarbonates), phosphates (including orthophosphates, tripolyphosphates and tetrapyrophosphates), silicates, borates (including, without limitation, hydrated pentaborates), aluminosilicates (both natural and synthetic zeolites), and mixtures thereof Organic builders are also suitable for use, and are selected from the group consisting of the alkali metal and ammonium sulfosuccinates, polyacrylates, polymaleates, copolymers of acrylic acid and maleic acid or maleic anhydride, citrates and mixtures thereof Depending upon the type of formulation, acidic builders, such as non-neutralized polycarboxylic acids, boric acid, and the like, may also be suibable. Examples of suitable propellants include organic (e.g., volatile organic solvents) and inorganic (e.g., compressed carbon dioxide) materials, such as those described in U.S. Pat. No. 4,652,389, particularly, at column 6, lines 15 through 54, which is incorporated herein by this reference. Additional disinfecting agents may include hydrogen peroxide or sodium hypochlorite.

Optional additives further include an insecticide, such as that available by the name Fipronil (5-amino-1-(2,6-dichloro-α,α,α-trifluoro-p-tolyl)-4-trifluoromethylsulphinylpyrazole-3-carbonitrile) from Rhone Poulenc, and that available by the name Hydramethylnon (listed as CAS-67485-29-4) from American Cyanamid; a fungicide, such as any fungicide defined by the Federal Insecticides, Fungicides and Rodenticides Act ("FIFRA", 7 U.S.C. Section 136 et seq., which is incorporated herein by this reference); a rodenticide, such as any rodenticide defined by FIFRA; and any mixture thereof

EXPERIMENTS AND RESULTS

Experiments were conducted to determine the antimicrobial efficacy of the inventive composition and to compare it to that of prior formulations, as described below.

In a first experiment, a formulation containing d-limonene and a quaternary ammonium compound, but lacking nerolidol, was prepared. The components of this formulation ("Formulation 1") and amounts of same in weight percentages relative to the formulation are set forth directly below.

Formulation 1

| Component | Weight Percent (%) |
|---|---|
| Quaternary Ammonium Compound[1] | 1.15 |
| d-Limonene | 2.50 |
| Dipropylene Glycol n-Butyl Ether | 1.00 |
| Isopropyl Alcohol | 4.90 |
| Linear Alcohol Ethoxylate $C_{10-12}$[2] | 1.38 |
| Linear Alcohol Ethoxylate $C_{10-12}$[3] | 2.55 |
| Fragrance | 0.00–1.00 |

-continued

Formulation 1

| Component | Weight Percent (%) |
|---|---|
| Dye | 0.00–1.00 |
| Deionized Water | Remainder |

[1] Dialkyl Dimethyl Ammonium Chloride
[2] 8 moles Ethoxylate
[3] 2.6 moles Ethoxylate Formulation 1 was then diluted 1:64 using 200 ppm hard water ("Dilution 1"). Dilution 1 was then tested against the microorganisms *Staphylococcus aureus* (ATCC 6538) and *Pseudomonas aeruginosa* (ATCC 15442), using a 5 percent soil load and an exposure time of 10 minutes. The test methods used were the use-dilution methods for testing disinfectants, namely, nos. 955.15 and 964.02, respectively, of *The Official Methods of Analysis of the Association of Official Analytical Chemists,* Fifteenth Edition (1990). The results of 60-carrier tests showed failures as to both of the microorganisms.

Thus, another Formulation 1 was prepared and diluted 1:64 using sterile distilled water ("Dilution 2"), as opposed to hard water. Dilution 2 was then tested against the microorganism *Pseudomonas aeruginosa* (ATCC 15442), using a 5 percent soil load and an exposure time of 10 minutes, according to the above-referenced use-dilution testing method no. 964.02. The results of a 20-carrier screening test showed 2 positives.

The above-described test results for Dilutions 1 and 2 are set forth in Table 3 below.

TABLE 3

| | Test Results No. Positive/No. Carriers) | |
|---|---|---|
| Dilution | Staphylococcus aureus | Pseudomonas aeruginosa |
| 1 | 2/60 | 45/60 |
| 2 | not tested | 2/20 |

While the distilled-water Dilution 2 out-performed the hard-water Dilution 1, it provided less than desirable results.

Experiments were then conducted with compositions containing nerolidol. That is, two new compositions were prepared, one containing Formulation 1 and 0.01 weight percent nerolidol relative to the composition and the other containing Formulation 1 and 0.02 weight percent nerolidol relative to the composition. The compositions were then diluted 1:64 using sterile distilled water to form "Composition 1" and "Composition 2", respectively. These compositions were then tested against the two microorganisms, *Staphylococcus aureus* (ATCC 6538) and *Pseudomonas aeruginosa* (ATCC 15442), using a 5 percent soil load and an exposure time of 10 minutes, in the manner set forth above. The test results of 60-carrier tests showed passing efficacy, or zero positives, against both microorganisms, as shown in Table 4.

TABLE 4

| Composition | Test Results (No. Positives/No. Carriers) | |
|---|---|---|
| | *Staphylococcus aureus* | *Pseudomonas aeruginosa* |
| 1 | 0/60 | 0/60 |
| 2 | 0/60 | 0/60 |

These results showed nerolidol to be an effective antimicrobial component in Compositions 1 and 2.

Nerolidol did not appear to be a particularly effective antimicrobial component when added to a commercial pine cleaner formulation, which contains pine oil, but no quaternary ammonium compound. That is, further experiments were conducted in which different amounts of nerolidol were added to two such formulations, which were then diluted 1:64 with sterile distilled water to provide Formulation 1 and Formulation 2 set forth in Table 5, containing nerolidol in an amount of 0.20 and 2.00 weight percent relative to the formulation, respectively.

Formulations 1 and 2 were then tested against three microorganisms, namely, *Salmonella choleraesuis, Staphylococcus aureus* and *Pseudomonas aeruginosa*, using a 5 percent soil load and an exposure time of 10 minutes. The test for the former microorganism was conducted according to use-dilution method for testing disinfectants, no. 955.14, of *The Official Methods of Analysis of the Association of Official Analytical Chemists*, Fifteenth Edition (1990), while the tests for the latter two microorganisms were conducted according to the above-referenced use-dilution methods nos. 955.15 and 964.02.

The results of 20-carrier screening tests showed failures for Formulation 1 as to the latter two microorganisms, and a failure for Formulation 2 as to the *Staphylococcus aureus* microorganism, as set forth in Table 5.

TABLE 5

| Formulation | Test Results (No. Positives/No. Carriers) | | |
|---|---|---|---|
| | *Salmonella choleraesuis* | *Staphylococcus aureus* | *Pseudomonas aeruginosa* |
| 1 | not tested | 6/20 | 6/20 |
| 2 | 0/20 | 5/20 | not tested |

Thus, unlike the inventive composition, pine cleaner formulations, which lack a quaternary ammonium compound, do not provide desirable disinfection results in the presence of nerolidol.

In further experiments, four compositions (Control, A, B, and C) having the components set forth in Table 6 were prepared for use in tests according to the methods described above.

TABLE 6

| Component | Comp'n | Wt.Pt.(%) |
|---|---|---|
| Quaternary Ammonium Compound[1]: | Control | 1.15 |
| | A | 1.15 |
| | B | 1.15 |
| | C | 0.87 |
| Nerolidol: | Control | 0.00 |
| | A | 0.01 |
| | B | 0.02 |
| | C | 0.05 |
| d-Limonene | ALL[2] | 2.50 |

TABLE 6-continued

| Component | Comp'n | Wt.Pt.(%) |
|---|---|---|
| DPnB | ALL | 1.00 |
| Isopropyl Alcohol | ALL | 4.00 |
| Linear Alcohol Ethoxylate $C_{10-12}$[3] | ALL | 3.60 |
| Linear Alcohol Ethoxylate $C_{10-12}$[4] | ALL | 2.25 |
| Fragrance | ALL | 0.00–1.00 |
| Dye | ALL | 0.00–1.00 |
| Deionized Water | ALL | Remainder |

[1]Dialkyl Dimethyl Ammonium Chloride
[2]All Compositions (Control, A, B, and C)
[3]8 moles Ethoxylate
[4]2.6 moles Ethoxylate The "Control Composition" included a quaternary ammonium compound, namely, dialkyl dimethyl ammonium chloride, at 1.15 weight percent relative to the composition, but no nerolidol. This Control Composition was tested and found to be ineffective as a disinfectant against *Pseudomonas aeroginosa*, as shown in Table 7 below. However, when nerolidol was added to this Control Composition at levels of 0.01 weight percent and 0.02 weight percent of the composition to form "Composition A" and "Composition B", respectively, both compositions proved to be effective as disinfectants as to this particular microorganism, inter alia, as shown in Table 7.

As described above, both Composition A and Composition B contained 1.15 weight percent of the quaternary ammonium compound component. However, in cleaning composition technology, quaternary ammonium compounds are known to cause undesirable toxicity and residue deposition. For example, such compounds are known to cause skin or eye irritation when present in sufficient amounts, such as amounts above about 1.0 weight percent relative to the composition. Thus, experiments were conducted to determine whether the amount of the quaternary ammonium compound could be reduced in compositions which are enhanced with nerolidol.

In these further experiments, it was determined that the amount of the quaternary ammonium compound component could be reduced to produce effective results in terms of disinfectancy as to one or more of the *Salmonella choleraesuis, Staphylococcus aureus* and *Pseudomonas aeruginosa* microorganisms. For example, "Composition C" containing the Control Formulation, 0.87 weight percent of dialkyl dimethyl ammonium chloride, 0.05 weight percent nerolidol, and a particular nonionic surfactant, Surfonic L 12-6 ($C_{10-12}$; 6 moles of EO) from Huntsman Chemical, was shown to be effective as a disinfectant as to *Salmonella choleraesuis* and *Staphylococcus aureus*, as shown in Table 7. In this Composition C, the nonionic surfactant, Surfonic L 12-6, was preferred solely for phase stability.

TABLE 7

| Composition | Test Results (No. Positives/No. Carriers) | | |
|---|---|---|---|
| | *Salmonella choleraesuis* | *Staphylococcus aureus* | *Pseudomonas aeruginosa* |
| Control | not tested | not tested | 2/20 |
| A | not tested | 0/60 | 0/20;0/60 |
| B | not tested | not tested | 0/20 |
| C | 0/30 | 0/30 | not tested |

The experimental results evidence the significantly enhanced antimicrobial efficacy, for example, disinfecting or sanitizing efficacy, of the inventive composition which includes at least one quaternary ammonium compound and nerolidol. This enhanced efficacy may be obtained using surprisingly small amounts of the enhancing or potentiating nerolidol. Further, this enhanced efficacy may be obtained using reduced amounts of quaternary ammonium compounds, as compared to amounts used in prior formulations. Thus, the inventive composition reduces or eliminates toxicity as to a user's skin or eyes and reduces or eliminates residue deposition, as compared to prior formulations containing quaternary ammonium compounds. Further, the inventive composition may be formulated quite simply and relatively inexpensively.

The inventive composition is especially effective in the disinfecting of a surface having certain microorganism deposits thereon, such as *Staphylococcus aureus, Pseudomonas aeruginosa,* and *Salmonella choleraesuis,* as demonstrated herein. The enhanced antimicrobial composition of the present invention is thus particularly suited for sanitizing or disinfecting applications, such as the sanitizing or disinfecting of hard surfaces.

Further experiments were conducted to determine the antimicrobial efficacy of the inventive composition, including at least one quaternary ammonium component and nerolidol, but omitting the preferred d-limonene cleaning solvent. As described above, d-limonene is used primarily for cleaning efficacy, and secondarily, for some degree of antimicrobial efficacy. Thus, it was surprisingly determined that the inventive composition, formulated without d-limonene, also showed enhanced antimicrobial efficacy.

Table 8 lists the components of the inventive composition, formulated without d-limonene, and the concentration ranges for same in approximate weight percentages (%) relative to the inventive composition, according to one embodiment. Table 9 lists the components of the inventive composition, formulated with pine oil, but without d-limonene, and the concentration ranges for same in approximate weight percentages (%) relative to the inventive composition, according to another embodiment.

TABLE 8

| Component | Weight Percent (%) |
| --- | --- |
| Quaternary Ammonium Compound[1] | 0.50–5.00 |
| Nerolidol | 0.01–2.00 |
| Dipropylene Glycol n-Butyl Ether | 0.00–7.50 |
| Isopropyl Alcohol | 1.00–10.00 |
| Linear Alcohol Ethoxylate $C_{10-12}$[2] | 0.25–8.00 |
| Linear Alcohol Ethoxylate $C_{10-12}$[3] | 1.50–10.00 |
| Water | Remainder |

[1]Dialkyl Dimethyl Ammonium Chloride
[2]8 moles Ethoxylate
[3]2.6 moles Ethoxylate The inventive compositions of Table 8 form microemulsions having an aqueous phase of from about 80.50 to about 98.49 weight percent relative to the composition and an oil phase of from about 1.51 to about 19.50 weight percent relative to the composition.

TABLE 9

| Component | Weight Percent (%) |
| --- | --- |
| Quaternary Ammonium Compound[1] | 0.50–5.00 |
| Nerolidol | 0.01–2.00 |
| Isopropyl Alcohol | 2.00–14.00 |
| Linear Alcohol Ethoxylate $C_{10-12}$[2] | 1.00–7.40 |
| Linear Alcohol Ethoxylate $C_{10-12}$[3] | 2.00–8.60 |
| Pine Oil | 3.00–21.00 |

TABLE 9-continued

| Component | Weight Percent (%) |
| --- | --- |
| Dye | 0.00–2.00 |
| Water | Remainder |

[1]Dialkyl Dimethyl Ammonium Chloride
[2]6 moles Ethoxylate
[3]2.6 moles Ethoxylate The inventive compositions of Table 9 form microemulsions having an aqueous phase of from about 68.40 to about 94.99 weight percent relative to the composition and an oil phase of from about 5.01 to about 31.60 weight percent relative to the composition.

For experiments conducted with the inventive compositions described in Table 8 and Table 9, Formulation 2 and Formulation 3, respectively, were prepared, as set forth below.

Formulation 2

| Component | Weight Percent (%) |
| --- | --- |
| Quaternary Ammonium Compound[1] | 0.87 |
| Nerolidol | 0.10 |
| Dipropylene Glycol n-Butyl Ether | 2.50 |
| Isopropyl Alcohol | 4.50 |
| Linear Alcohol Ethoxylate $C_{10-12}$[2] | 2.25 |
| Linear Alcohol Ethoxylate $C_{10-12}$[3] | 3.50 |
| Water | Remainder |

[1]Dialkyl Dimethyl Ammonium Chloride
[2]6 moles Ethoxylate
[3]2.6 moles Ethoxylate The microemulsion of Formulation 2 had an aqueous phase of about 93.90 weight percent relative to the composition and an oil phase of about 6.10 weight percent relative to the composition.

Formulation 3

| Component | Weight Percent (%) |
| --- | --- |
| Quaternary Ammonium Compound[1] | 1.25 |
| Nerolidol | 0.10 |
| Isopropyl Alcohol | 7.00 |
| Linear Alcohol Ethoxylate $C_{10-12}$[2] | 4.20 |
| Linear Alcohol Ethoxylate $C_{10-12}$[3] | 4.80 |
| Pine Oil | 12.0 |
| Dye | 0.0025 |
| Water | Remainder |

[1]Dialkyl Dimethyl Ammonium Chloride
[2]6 moles Ethoxylate
[3]2.6 moles Ethoxylate The microemulsion of Formulation 3 had an aqueous phase of about 83.10 weight percent relative to the composition and an oil phase of about 16.90 weight percent relative to the composition.

Also formulated were Formulation 2A and a Formulation 3A, both of which lacked the nerolidol component. That is, Formulation 2A was formulated in the same manner as Formulation 2, excepting the nerolidol component, and Formulation 3A was formulated in the same manner as Formulation 2, excepting the nerolidol component.

Formulations 2, 2A, 3, and 3A were then diluted 1:64 using sterile distilled water, to form Diluted Formulations 2, 2A, 3, and 3A, respectively. These Diluted Formulations were then tested against the microorganism, *Pseudomonas aeruginosa* (ATCC 15442), using a 5 percent soil load and an exposure time of 10 minutes, in the manner set forth previously herein. The results are set forth in Table 10.

TABLE 10

| Diluted Formulation | Test Results (No. Positives/No. Carriers) *Pseudomonas aeruginosa* |
|---|---|
| 2 | 1/60 |
| 2A | 8/60 |
| 3 | 1/60 |
| 3A | 5/60 |

That is, Diluted Formulations 2 and 3 passed the antimicrobial efficacy tests against *Pseudomonas aeruginosa* (1/60 is required for a passing result), while Diluted Formulations 2A and 3A, both of which lacked the nerolidol component, failed the antimicrobial efficacy tests against *Pseudomonas aeruginosa*.

These further experimental results evidence the enhanced antimicrobial efficacy of the invention composition in the absence of the preferred d-limonene cleaning solvent. Such results were obtained for inventive compositions including either DPnB or pine oil as a cleaning solvent.

The inventive compositions described in Tables 8 and 9 may be formulated as previously described with respect to the preferred embodiments, with the exception of the otherwise preferred d-limonene component. These inventive compositions provide features and advantages such as those previously described with respect to the preferred embodiments. Thus, while the enhanced antimicrobial composition preferably includes a d-limonene component, such component is not required in the inventive composition.

It is to be understood that while the invention has been described above in conjunction with preferred specific embodiments, the description and examples are intended to illustrate and not to limit the scope of the invention, which is defined by the scope of the appended claims.

What is claimed is:

1. An antimicrobial composition comprising:
   d-limonene is a first amount from about 1.00 to about 5.00 weight percent relative to the composition;
   at least one quaternary ammonium compound in a second amount from about 0.50 to about 5.00 weight percent relative to the composition; and nerolidol in a third amount for antimicrobial efficacy, said third amount being at least 0.01 weight percent to about 2.00 weight percent relative to the composition.

2. The composition of claim 1, further comprising an oil-phase solubility enhancer or coupling agent, a surfactant, a solvent, water, a disinfectant, a hydrotrope, a chelating agent, a builder, a fragrance, a dye, a pigment, a coloring agent, other than d-limonene, or any combination thereof.

3. The composition of claim 2, wherein the oil-phase solubility enhancer is selected from a group consisting of an alkanol, a $C_{1-6}$ diol, a $C_{1-10}$ alkylene glycol ether, and any mixture thereof.

4. The composition of claim 3, wherein the oil-phase solubility enhancer is isopropyl alcohol.

5. The composition of claim 2, wherein the surfactant is a nonionic surfactant.

6. The composition of claim 5, wherein the nonionic surfactant is selected from a group consisting of a linear alkoxylated alcohol, a branched alkoxylated alcohol, an alkoxylated alkylphenol, and any mixture thereof.

7. The composition of claim 6, wherein the nonionic surfactant is a linear alcohol ethoxylate.

8. The composition of claim 2, wherein the solvent is selected from a group consisting of a terpene derivative, ethylene glycol monobutyl ether, ethylene glycol monopropyl ether, propylene glycol n-propyl ether, propylene glycol monobutyl ether, diethylene glycol n-butyl ether, dipropylene glycol methyl ether, dipropylene glycol n-butyl ether, and any mixture thereof.

9. The composition of claim 2, wherein the solvent has cleaning or antimicrobial efficacy.

10. The composition of claim 9, wherein the solvent is selected from a group consisting of dipropylene glycol n-butyl ether, a pine-oil solvent, and any mixture thereof.

11. The composition of claim 1, wherein the composition is a microemulsion.

* * * * *